(12) United States Patent  (10) Patent No.: US 8,833,372 B2
Han et al.  (45) Date of Patent: Sep. 16, 2014

(54) INTEGRATED MASK AND PRONGS FOR NASAL CPAP

(75) Inventors: Steve Han, Upland, CA (US); Steve Duquette, Laguna Niguel, CA (US); Harold Miller, Upland, CA (US)

(73) Assignee: Carefusion 207, Inc., San Diego, CA (US)

( * ) Notice: Subject to any disclaimer, the term of this patent is extended or adjusted under 35 U.S.C. 154(b) by 1563 days.

(21) Appl. No.: 11/807,513

(22) Filed: May 29, 2007

(65) Prior Publication Data

US 2008/0295846 A1 Dec. 4, 2008

(51) Int. Cl.
*A62B 18/02* (2006.01)
*A61M 16/06* (2006.01)

(52) U.S. Cl.
CPC ........... *A61M 16/06* (2013.01); *A61M 16/0666* (2013.01); *A61M 2210/0618* (2013.01)
USPC ............ 128/207.13; 128/206.21; 128/205.25; 128/204.18

(58) Field of Classification Search
USPC ............. 128/207.13, 200.24, 201.22, 204.18, 128/205.25, 206.21, 206.24, 207.18
See application file for complete search history.

(56) References Cited

U.S. PATENT DOCUMENTS

| 5,193,532 | A  | * | 3/1993  | Moa et al. ................ 128/204.25 |
| 6,644,315 | B2 |   | 11/2003 | Ziaee |
| 7,556,043 | B2 | * | 7/2009  | Ho et al. .................. 128/207.18 |
| 7,578,294 | B2 | * | 8/2009  | Pierro et al. ............. 128/207.13 |
| 7,640,934 | B2 | * | 1/2010  | Zollinger et al. ........ 128/207.18 |
| 7,762,258 | B2 | * | 7/2010  | Zollinger et al. ........ 128/206.24 |
| 2002/0170928 | A1 |   | 11/2002 | Grychowski et al. |
| 2003/0200970 | A1 | * | 10/2003 | Stenzler et al. .......... 128/207.18 |
| 2004/0182398 | A1 |   | 9/2004  | Sprinkle et al. |
| 2006/0078506 | A1 | * | 4/2006  | Niven et al. .................... 424/45 |
| 2007/0074724 | A1 |   | 4/2007  | Duquette et al. |
| 2007/0089749 | A1 |   | 4/2007  | Ho et al. |
| 2007/0125384 | A1 | * | 6/2007  | Zollinger et al. ........ 128/206.24 |

FOREIGN PATENT DOCUMENTS

WO WO 2005/063328 7/2005
WO WO 2007/050557 5/2007

OTHER PUBLICATIONS

Office Action for JP Patent Application No. 2010/510450 dated Oct. 30, 2012.
Office Action for JP Patent Application No. 2010/510450 dated Sep. 3, 2013.

* cited by examiner

*Primary Examiner* — Justine Yu
*Assistant Examiner* — Colin W Stuart
(74) *Attorney, Agent, or Firm* — McDermott Will & Emery LLP

(57) ABSTRACT

An integrated nasal mask is adapted for delivering gas to a patient and comprises a mask body and a pair of elongate nostril-engaging stems. The mask body is generally triangularly shaped and includes a nasal opening sized and configured to substantially envelope a patient's nose. The nasal opening opens to a nasal cavity. The nostril-engaging stems extend outwardly from the nasal cavity. Each one of the stems defines a fluid passageway for delivering gas to the patient's nose and for allowing discharge of exhalation gasses during the exhalation phase of the breathing cycle.

18 Claims, 4 Drawing Sheets

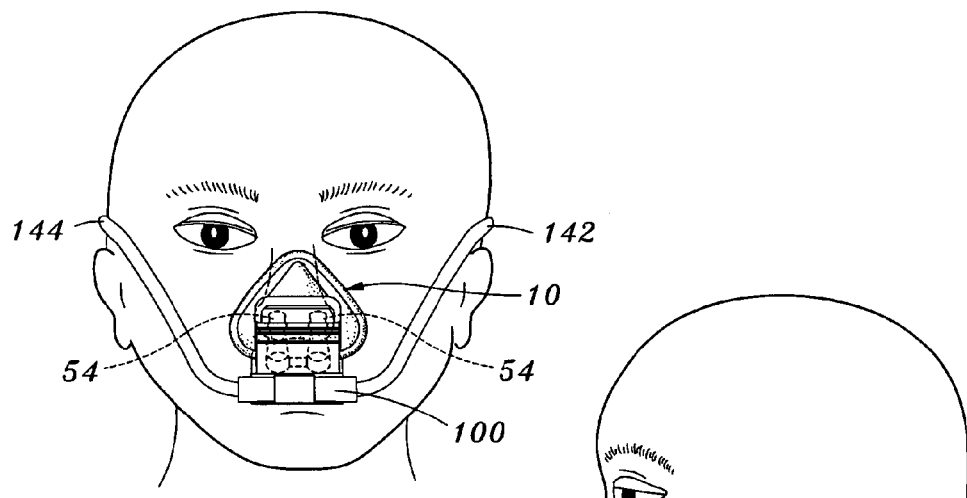
Fig. 1
Fig. 2
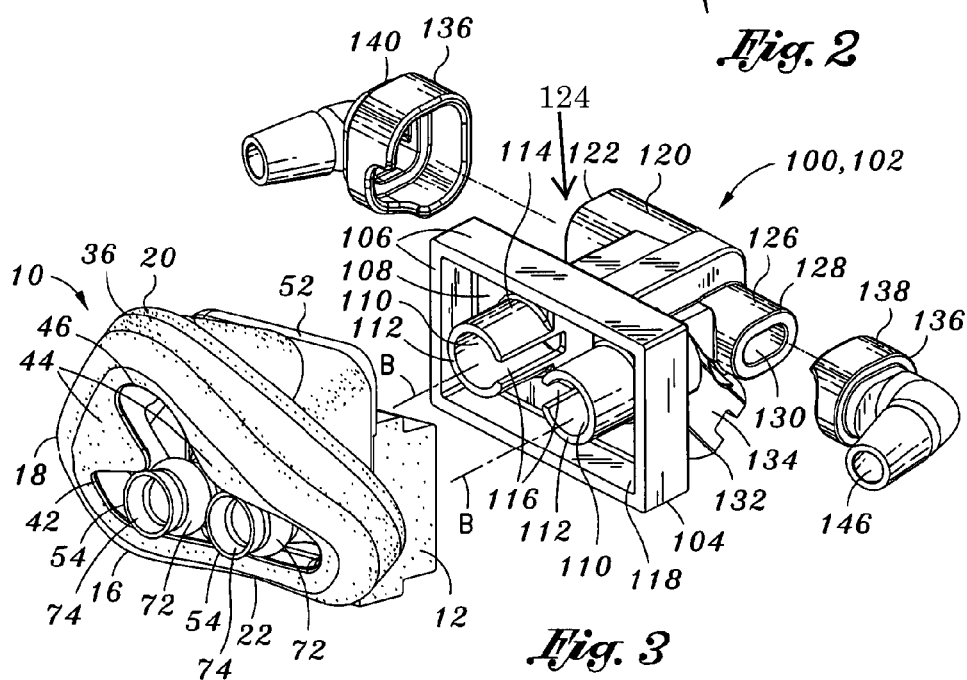
Fig. 3

INTEGRATED MASK AND PRONGS FOR NASAL CPAP

CROSS-REFERENCE TO RELATED APPLICATIONS (Not Applicable)

STATEMENT RE: FEDERALLY SPONSORED RESEARCH/DEVELOPMENT (Not Applicable)

BACKGROUND

The present invention relates generally to breathing devices and, more particularly, to a uniquely-configured nasal mask which is specifically adapted to provide improved sealing to the nasal area of a patient in order to enhance the treatment of certain respiratory conditions.

The use of a breathing apparatus upon respiratory-impaired patients is well known. Generally, such apparatuses assist in patient breathing by allowing proper exchange of inhaled and exhaled gas while providing pressurized gasses to the patient's lungs so as to prevent lung collapse during breathing. In one embodiment, such breathing apparatuses allow spontaneous breathing of the patient while sustaining the application of continuous positive airway pressure (CPAP) to the patient's lungs. CPAP therapy functions primarily to establish an open airway in the patient by delivering continuous flow of gasses such as humidified oxygen in combination with other gasses.

CPAP devices typically include a gas source such as a blower unit which is connected to the user interface by a tubing member such as a gas supply tube. The user interface can be configured for invasive or non-invasive CPAP therapy. For invasive CPAP therapy, gas may be delivered to the patient via a tracheal tube or a pair of nasopharyngeal prongs. For non-invasive CPAP therapy, gas may be delivered to the patient via a conventional nasal mask or a pair of nasal prongs. In either configuration, gas is ideally delivered to the patient at a constant and stable pressure.

Both the nasal mask and nasal prongs are specifically configured to deliver a flow of pressurized gas to the nasal area of the patient. With nasal prongs, pressurized gas is preferably directed into the patient's nostrils through a pair of nostril-engaging prongs or stems which are typically configured to anatomically conform to the interior of the patient's nostrils. Nasal masks as conventionally known are generally triangularly-shaped and, ideally, are sized and configured to substantially envelope and seal around the patient's nose.

The ability to supply pressurized gas to the airways of the patient on a constant basis and at a stable pressure is critical in the effectiveness of CPAP ventilation. The ability to provide constant CPAP therapy is especially important in treating certain respiratory conditions in neonate and infants such as respiratory distress syndrome (RDS). Nasal CPAP therapy is proven as an effective treatment for RSD by developing and restoring functional respiratory capacity through the supply of constant pressure to the neonates airway. Furthermore, nasal CPAP is one of the more easily-administered and one of the best-tolerated respiratory treatment methods amongst infants.

Unfortunately, despite it effectiveness, conventional nasal masks and nasal prongs possess certain deficiencies which detract from their overall utility. One of the most common deficiencies associated with conventional nasal CPAP is improper administration thereof due to poor sealing of nasal masks and nasal prongs at the patient. The improper administration of nasal CPAP can result in serious injuries and complications when misapplied over extended periods of time. For example, nasal masks, and/or nasal prongs may be secured to the patient using a system of straps which are secured around the patient's head in order to maintain position of the nasal mask and/or nasal prongs against the patient's nose such that a proper seal is maintained.

If adjusted too tightly, the straps can create excessive pressure against the patient's face which is particularly problematic for nasal prongs. More particularly, if the straps are adjusted too tightly around the patient's head, the nasal prongs may be forced upwardly into the patient's nostrils which can result in irritation of the tender mucus tissue lining the patient's nostrils. Over extended periods of time (i.e. hours up to days), excessive pressure exerted by nasal prongs against the nasal septum can cause septal erosion as well as cause damage to the lateral walls of the nostrils. In addition, prolonged use of ill-fitting nasal prongs can result in nasal flaring, nasal snubbing and other injuries. An overly-tightened nasal mask can also result in similar nasal trauma including the above-mentioned injury associated with septal erosion.

As was earlier mentioned, the ability to apply CPAP therapy at a constant pressure over extended periods of time is critical in treating certain patients such as premature infants who are especially prone to RDS. The above-mentioned problems associated with an overly-tightened nasal mask or nasal prongs may result from an attempt by caregivers (e.g., family members, nurses) to provide an effective seal against the patient's face to prevent leakage of gas. As is well known in the art, excessively low pressure at the patient can drastically reduce the effectiveness of CPAP therapy.

Low pressure at the patient can result from leaks as a result of improper fitment or positioning of the nasal mask and/or nasal prongs against the patient. Leaks can also be generated at the patient as a result of normal patient movement. The ability to provide leak-free sealing can also result from the relatively wide range of facial structures and sizes amongst different patents and the limited number of commercially-available mask configurations that can accommodate the different facial structures and sizes. Leakage can also be a result from normal patient movements. In particular, infants who make frequent jerking and shaking movements as a part of their physical development can cause difficulty in maintaining a comfortable and leak-free seal of a nasal mask or nasal prongs.

As can be seen, there exists a need in the art for a nasal mask and/or nasal prongs that can provide an effective seal against the patient's face without excessive leakage. Furthermore, there exists a need in the art for a nasal mask which provides such effective sealing without the imposition of undue pressure against the patient's face. Additionally, there exists a need in the art for a nasal mask capable of anatomically conforming to a wide range of facial structures and sizes without leakage. Finally, there exists a need in the art for a nasal mask which is of simple construction, low cost and which is conveniently installable and which maintains a leak-free seal despite normal patient movement.

BRIEF SUMMARY

The present invention specifically addresses and alleviates the above-referenced deficiencies associated with nasal masks and nasal prongs of the prior More particularly, the present invention is an integrated nasal mask which is adapted for delivering gas to a patient with reduced risk of leakage. More specifically, the integrated nasal mask combines a mask body with a pair of nostril-engaging stems. The mask body is generally triangularly-shaped and includes a nasal opening which is sized and configured to substantially envelope and seal against a patient's nose.

The nostril-engaging stems extend outwardly from the nasal cavity and are configured to sealingly engage opposing sides of the patient's nostrils. Each one of the nostril-engaging stems defines a fluid passageway which is adapted for delivering gas to the patient's nose as well as providing a pathway for exhaled gasses during the exhalation phase of the breathing cycle.

The nasal mask includes a mask shoulder which has a generally tapering wall thickness in order to increase its ability to conform to the patient's facial structure. The mask shoulder extends around a periphery of the nasal opening. The mask body also includes a mask base wall and mask sidewalls which extend outwardly from the mask base wall. The mask sidewalls may also have a tapering wall thickness such that the mask body may better conform to the patient's face.

Additionally, the mask shoulder includes a sealing flange extending therearound and includes a pair of flapper portions disposed on opposing sides of the mask body and which are integrated into the sealing flange. Each one of the flapper portions is preferably configured to sealingly engage opposing exterior sides of the patient's nose in an area adjacent the patient's nostrils.

Each one of the nostril-engaging stems has proximal and distal ends with the proximal end being engaged to the nasal cavity. The distal end terminates at a flare portion which is sized and configured to sealingly engage the patient's nostrils. Each one of the stems may further include a bulb portion located adjacent to the flare portion and which is configured to facilitate lateral deflection of the flare portion in order to better conform to different nostril spacings between different patients. Lateral deflection of the flare portion is also facilitated by an annular notch formed on one of opposing ends of the bulb portion to allow the bulb portion to act as a bellows and further facilitate relative movement of the flare portion to better conform to the inner anatomical structure of the patient's nostrils.

The nasal mask may be adapted to be engageable to a universal interface having a well portion wherein an interface portion of the nasal mask may frictionally engage the well portion. The universal interface preferably includes a pair of spaced patient ports which are sized and configured to be insertable into the fluid passageways defined by the nostril-engaging stems. The universal interface is preferably adapted to enhance CPAP therapy to the patient when used with a standard ventilator. More specifically, the universal interface acts as a flow generator which is adapted to reduce the work of breathing during CPAP therapy using a reduced supply gas pressure.

The universal interface that may be used with the nasal mask is similar to that which is disclosed in U.S. patent application Ser. No. 11/241,303 entitled VENTURI GEOMETRY DESIGN FOR FLOW-GENERATOR PATIENT CIRCUIT, filed Sep. 30, 2005 by Duquette et al., the entire contents of which is incorporated by reference herein. Due to its internal geometry, the universal interface minimizes pressure resistance during the inhalation and exhalation phases of breathing.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a frontal view of an integrated nasal mask as installed on a patient and comprising a mask body and pair of nostril-engaging stems;

FIG. 2 is a side view of the nasal mask illustrating the pair of nostril-engaging stems engaged to the nares of the patient and further illustrating the mask body engaged to and encircling the patient's nose;

FIG. 3 is an exploded perspective view of an exemplary embodiment of a universal interface to which the integrated nasal mask may be engaged;

DETAILED DESCRIPTION

Figure 4:
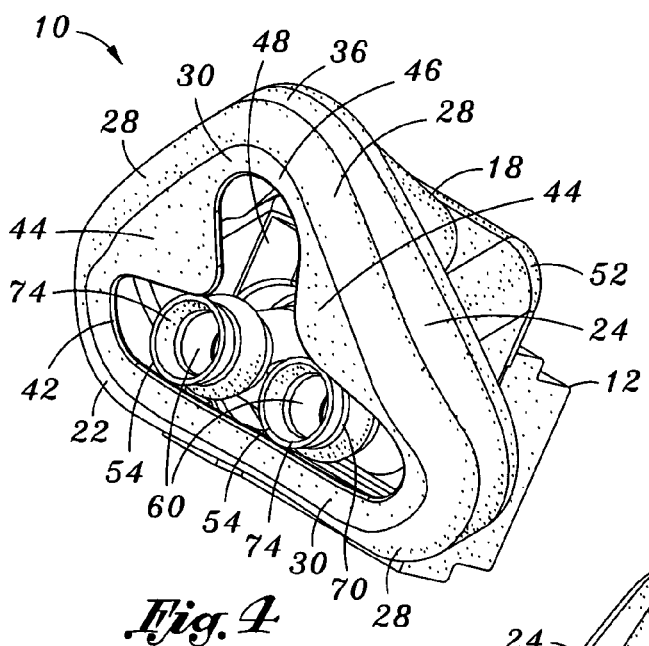
FIG. 4 is a perspective view of the integrated nasal mask illustrating the triangular shape of the mask body.

Referring now to the drawings wherein the showings are for purposes of illustrating preferred embodiments of the present invention and not for purposes of limiting the same, shown in the figures is an integrated nasal mask 10 specifically adapted for delivering gas to a patient with improved sealing effectiveness around the patient's nose. In its broadest sense, the integrated nasal mask 10 comprises a mask body 18 configured to envelope a patient's nose and a pair of nostril-engaging stems 54 sized and configured to sealingly engage with the patient's nostrils.

Advantageously, the nasal mask 10 is suitable for providing various forms of respiratory therapy including nasal CPAP therapy. For example, as illustrated in FIGS. 1-3, the nasal mask 10 may be configured to be interchangeably or removably mountable to a universal interface 100 such as may be fitted with a supply tube 144 and a pressure tube 142 extending outwardly from opposed sides of the universal interface 100 and extending around the patient's head. In this regard, the universal interface 100 may be adapted to provide CPAP therapy to the patient when the interface is used with a standard ventilator.

In an exemplary embodiment, the universal interface 100 may be similar to that which is disclosed and illustrated in the above-mentioned U.S. patent application Ser. No. 11/241,303 entitled VENTURI GEOMETRY DESIGNED FOR FLOW-GENERATOR PATIENT CIRCUIT. The universal interface 100 disclosed in the Duquette reference is configured to increase efficiency and reduce the work of breathing by the patient by reducing the required supply pressure in providing a constant positive pressure within the patient's airway. Furthermore, as mentioned above, the universal interface 100 disclosed in the Duquette reference is specifically configured to minimize pressure resistance during inhalation and exhalation phases of breathing.

As illustrated in FIG. 3, the universal interface 100 may include an interface body 102 having a supply fitting 136 and a pressure fitting 140 disposed on opposed sides of the interface body 102. Each of the supply and pressure fittings 136, 140 may include a flange 138 to facilitate connection thereof to the interface body 102. FIGS. 1-2 illustrate a supply tube 144 extending from the supply fitting 136 on one side of the universal interface 100 to supply gas from a gas source 146 to the patient. A pressure tube 142 may also be extended from the pressure fitting 140 on the opposing side of the universal interface 100 and is provided to allow for a means of measuring pressure at the patient during breathing.

Such pressure measurement may be facilitated by a pressure transducer or other pressure measurement device. The interface body 102 may include a spaced pair of breathing passageways 110 having a corresponding pair of supply passageways 130 fluidly connected thereto and having a pair of exhalation passageways fluidly connected to the breathing passageways 110. Each one of the breathing passageways 110 in the universal interface 100 is comprised of a patient passageway 114 that terminates at a patient port 112 disposed near a well portion 104 of the universal interface 100 as illustrated in FIG. 3.

The patient passageway 114 supplies gas to the patient while exhalation passageways expel gas from the patient during the expiration phase of the breathing cycle. The patient passageways 114 are interconnected to a supply manifold 126 via the corresponding pair of supply passageways 130. The supply manifold 126 splits fluid flow from the supply tube 144 into each of the patient passageways 114. The interface body 102 includes a pressure manifold 120 which exits at an exhalation port 134 and which allows for pressure measurement at the patient. The pressure passageway 124 extends from the pressure port 122 to a well opening 118 formed in the well portion 104 of the universal interface 100. The patient ports 112 allow pressure measurement at the patient due to the inclusion of an opposing pair of interface slots 116 which are disposed and positioned complimentary to a corresponding mask slot 14 formed in an interface portion 12 of the nasal mask 10.

The various functional aspects of the interface body 102 (i.e., pressure manifold 120, supply manifold 126, exhalation manifold 132, breathing passageways 110) are preferably integrally formed in the interface body 102. In addition, the well sidewalls 106 and well basewall 108 which collectively define the well opening 118 are also preferably integrally formed with the interface body 102 as are the patient ports 112 which extend outwardly from the well basewall 108 and into which the fluid passageways 60 of the nasal mask 10 are insertable.

Referring to FIG. 3, in one embodiment, the nasal mask 10 is preferably configured to be removably engageable to the universal interface 100 such as via frictional fit of a patient portion 16 of the nasal mask 10 within the well portion 104 of the universal interface 100. However, it should be noted that the nasal mask 10 may be used in conjunction with alternative embodiments of the universal interface 100 other than that which is shown in FIG. 3. Furthermore, it is contemplated that the pressure and supply tubes 142, 144 illustrated as extending from the universal interface 100 in FIGS. 1 and 2 may be directly coupled to the nasal mask 10.

Figure 5:
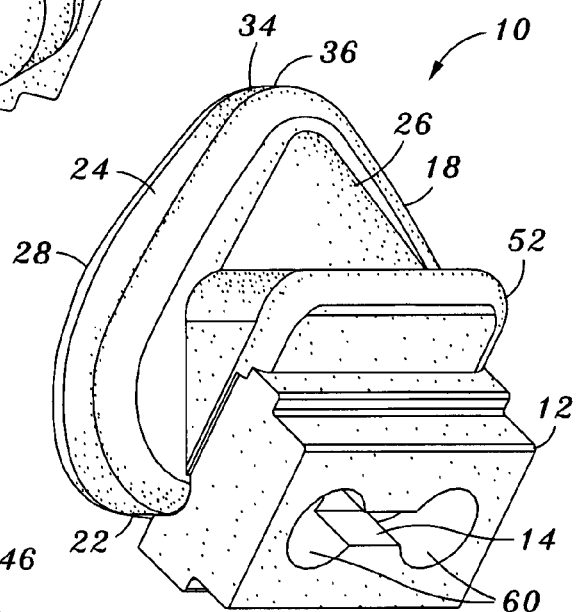
FIG. 5 is a perspective view of an aft side of the nasal mask illustrating an interface portion thereof configured to engage the universal interface illustrated in FIG. 3 and illustrating the mask body being secured to interface portion by a connecting web.
Figure 6:
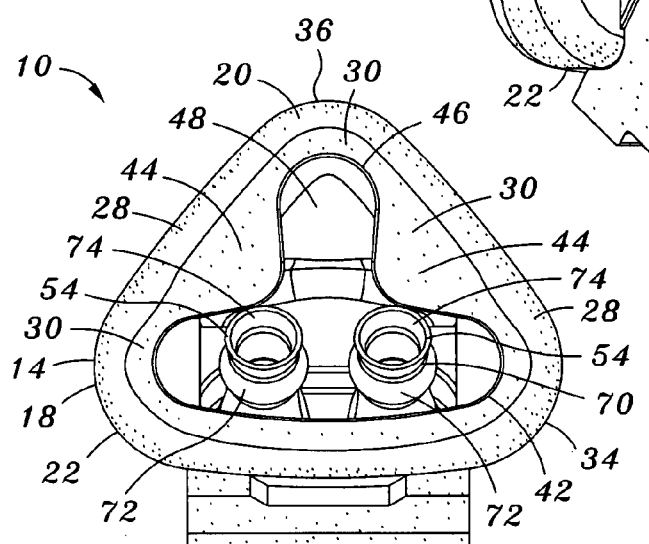
FIG. 6 is a front view of the nasal mask illustrating a nasal opening defining an entrance to a nasal cavity and through which the pair of nostril engaging stems protrude.

Referring now more particularly to FIGS. 4-6, the nasal mask 10 may optionally include the interface portion 12 which includes the pair of fluid passageways 60 into which are inserted the corresponding pair of patient ports 112 of the universal interface 100. In this regard, the interface portion 12 of the nasal mask 10 may have a generally rectangular shape formed complimentary to the generally rectangular shape of the well opening 118. Optionally, the interface portion 12 may include a step on upper and/or lower sides of the interface portion 12 to facilitate engagement of the nasal mask 10 to the universal interface 100.

Figure 7:
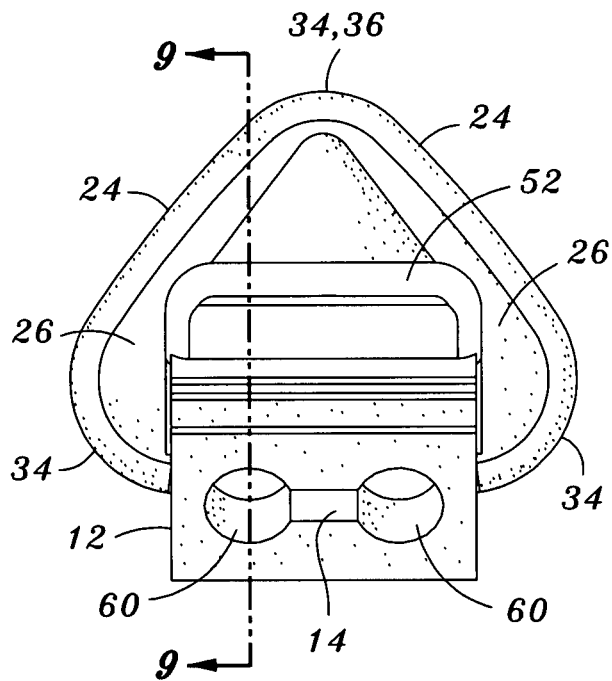
FIG. 7 is an aft view of the nasal mask illustrating a pair of fluid passageways which extend through the nostril-engaging stems and which terminate at the interface portion on one end.

Referring briefly to FIG. 7, shown is a front view of the interface portion 12 illustrating the pair of fluid passageways 60 which are preferably configured complimentary to (i.e., in spacing and diameter) of the patient ports 112 extending from the well opening 118 of the universal interface 100. Also preferably included in the interface portion 12 of the nasal mask 10 is a mask slot 14 which is configured complimentary to the pair of interface slots 116 formed in respective ones of the patient ports 112 of the universal interface 100. The interface slots 116 and mask slot 14 cooperate to allow exhaled gas to flow into the exhalation manifold 132 of the universal interface 100 for measurement thereof as is described in greater detail in U.S. patent application Ser. No. 11/241,303 entitled VENTURI GEOMETRY DESIGN FOR FLOW-GENERATOR PATIENT CIRCUIT.

Referring briefly to FIG. 4, shown is a perspective view of a front side of the nasal mask 10 illustrating the mask body 18 which defines a nasal cavity 48 into which the patient's nose is adapted to fit. Further included in the integrated nasal mask 10 is at least one and, more preferably, the pair of generally elongate nostril-engaging stems 54 which extend outwardly from the nasal cavity 48. Each one of the stems 54 defines the above-mentioned fluid passageway 60 which is adapted for delivering gas to the patient's nose and through which exhaled gas may be expelled.

Advantageously, the unique combination of the nasal mask 10 integrated with the nostril-engaging stems 54 provides a redundant sealing mechanism. More particularly, the combination of the mask body 18 sealing around the periphery of the patient's nose with the nostril-engaging stems 54 sealingly engaging the patient's nares prevents complete loss of sealing when one of the mask body 18 or nostril-engaging stems 54 becomes dislodged. For example, when the integrated nasal mask 10 is worn by a sleeper with active sleep patterns, the nostril-engaging stem 54 maintains sealing engagement with the patient's nares despite dislodgment of the mask body 18 from the periphery of the patient's nose as may occur if the nasal mask 10 contacts a pillow or other obstacle as a result of restlessness of the patient.

Referring still to FIG. 4, the mask body 18 may define a generally triangular shape having three corners 34 and may include a nasal opening 42 which is preferably sized and configured to substantially envelope a patient's nose. In this regard, it is contemplated that the mask body 18 may be provided in a variety of different sizes and shapes in order to accommodate a variety of patients with differing facial structures and differing sizes. For example, the nasal mask 10 may be provided in a range of sized to fit neonates up to adults.

Furthermore, it is contemplated that the nasal cavity 48 is provideable in a variety of sizes in order to fit differing nose structures such that the tip of the patient's nose does not come into contact with the nasal cavity 48. By providing the mask body 18 in a variety of sizes, proper fit and sealing engagement of the mask body 18 is possible without overly tightening the mask which can result in the above-described nasal trauma and patient discomfort.

Referring to FIGS. 4-6, the mask body 18 preferably includes a mask shoulder 28 which extends along a periphery of the nasal opening 42. The mask shoulder 28 has a generally curved cross-sectional shape extending upwardly from a mask sidewall 24. The mask body 18 further comprises a mask basewall 26 best seen in FIG. 5 and from which the mask sidewalls 24 extend. The mask basewall 26 is interconnected to the interface portion 12 of the nasal mask 10 by means of a connecting web 52 which is formed as a generally wedge-shaped structure having a generally hollow configuration as best seen in FIG. 9.

Figure 9:
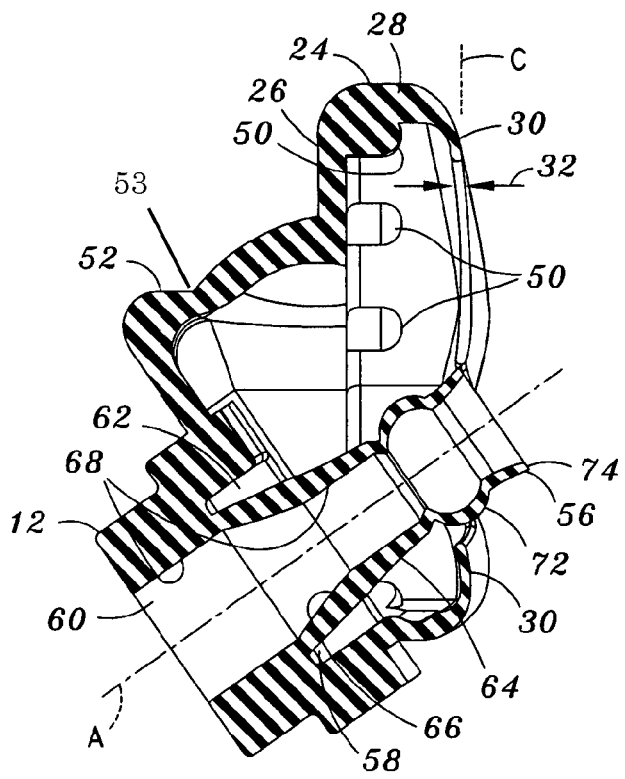
FIG. 9 is a cross-sectional view taken along lines 9-9 of FIG. 7 and illustrating the geometry of the nostril-engaging stems including a bulb portion transitioning into a flare portion.

Referring more particularly to FIG. 9, the connecting web 52 has a generally thickened wall structure in relation to the wall thickness 32 at the mask shoulder 28. Furthermore, the connecting web 52 may include a generally curved or convex-shaped upper wall having a lateral notch formed thereacross in order to facilitate flexing of the connecting web 52. By configuring the connecting web 52 to possess a certain degree of flexibility, tilting movement of the interface portion 12 relative to the mask sidewall 24 and mask shoulder 28 is facilitated.

Such tilting movement may be the result of up-and-down movement of the user interface or as a result of pulling or tugging on the pressure and/or supply tubes 142, 144 illustrated in FIGS. 1 and 2. The capability of the interface portion to move relative to the mask shoulder 28 minimizes the risk of loss of sealing engagement of the nasal mask 10. In addition, the connecting web 52 minimizes the risk of patient injury as a result of undue pressure of the nasal mask 10 on the patient's face.

For example, an upwardly-directed force imposed on the universal interface 100 may result in pressure points exerted by the corner 34 or apex 36 at the upper end 20 of the nasal mask 10 upon the patient's nasal bridge. In extreme cases, this excessive pressure may lead to contusions or other injuries over time. In another example, a downwardly directed force applied at the universal interface 100 may place excessive pressure of a lower end 22 of the mask body 18 on the patient's nasal septum which can lead to septal erosion over time. However, by providing a degree of flexibility to the connecting web 52, rotational movement of the interface portion 12 relative to the mask shoulder 28 is allowed which thereby minimizes the placement of excessive pressure on the patient's face.

Figure 8:
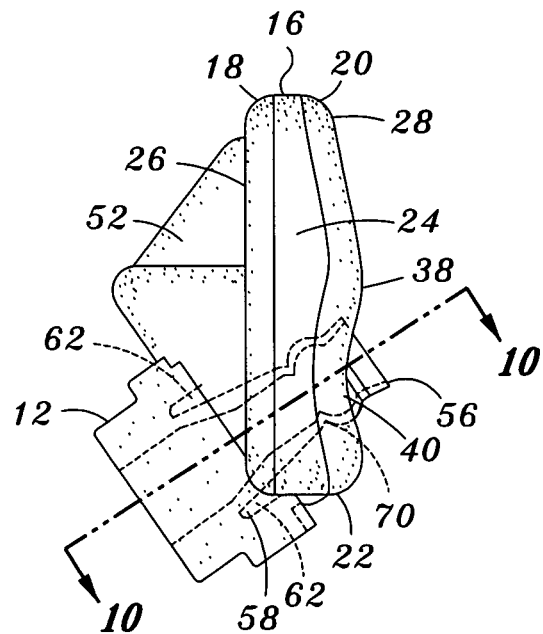
FIG. 8 is a side view of the nasal mask illustrating a contour formed in the mask body for conforming to a normal facial structure of a patient.

Referring now particularly to FIG. 8, shown is the mask body 18 wherein the mask shoulder 28 is preferably configured to anatomically conform to the contour of the patient's face. In this regard, the mask shoulder 28 may be provided with a protrusion 38 area and depression 40 area to accommodate the slightly protruding cheek portion adjacent the patient's nose on either side thereof. In this regard, the protrusion 38 and depression 40 are adapted to minimize pressure points of the nasal mask 10 on the patient's face. Optionally, the protrusion 38 and/or depression 40 areas of the mask shoulder 28 may be either entirely eliminated or may be biased toward one of upper and lower ends 20, 22 of the mask body 18.

Figure 10:
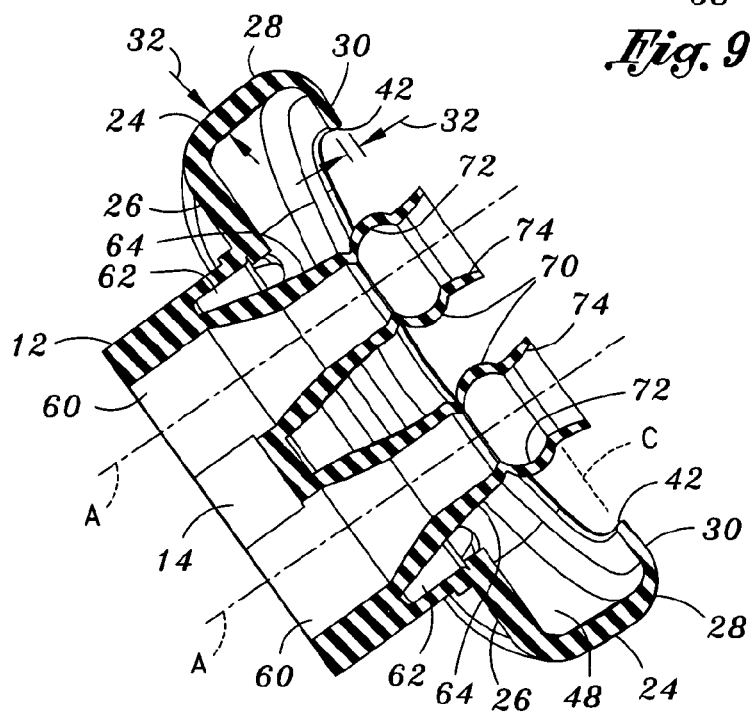
FIG. 10 is a cross-sectional view of the nasal mask taken along lines 10-10 of FIG. 8 and further illustrating a decreasing wall thickness of the mask body from a mask side wall through the mask shoulder and terminating at a sealing flange.

Referring now to FIGS. 9-10, shown are cross-sectional views of the nasal mask 10 illustrating the generally tapering wall thickness 32 from the mask sidewalls 24 to the mask shoulder 28 which terminates at a sealing flange 30 extending around the mask shoulder 28. The ability of the mask body 18 to conform to the patient's facial structure is further enhanced by tailoring the local wall thickness 32 as illustrated in FIGS. 9 and 10 such that the mask shoulder 28 and sealing flange 30 better accommodate facial features. Furthermore, the tapering wall thickness 32 provides a cushioning effect which enhances patient comfort.

Although shown as a gradual taper from the mask sidewalls 24 to the sealing flange 30, it is contemplated that the reducing wall thickness 32 may be provided in step form. Conformal sealing of the nasal mask 10 is enhanced by tailoring the wall thickness 32 to provide a desired degree of flexibility to the mask shoulder 28 for better sealing. The nasal cavity 48 is preferably sized to completely contain or envelope the patient's nose with sufficient clearance with the patient's nose tip. However, the geometry of the mask is also preferably configured to minimize dead space to better facilitate removal of $CO_2$ from the nasal cavity 48 during the patient's exhalation phase.

Referring briefly now to FIG. 6, shown is a pair of flapper portions 44 of the sealing flange 30 which are disposed on opposing sides of the mask body 18. The flapper portions 44 are specifically configured to sealingly engage opposing sides of the patient's nose. More specifically, each one of the flapper portions 44 is configured to engage an area on an exterior of the patient's nostrils which, for many patients, generally defines a recessed area of the nose. In this regard, the flapper portions 44 and the nose cutout 46 partially defined by the flapper portions 44 may prevent air leakage caused by malpositioning or unwanted movement of the universal interface 100 and which can result in eye irritation as a result of pressurized gas leaking around the nostrils or nasal bridge and flowing into the patient's eyes. Each of the flapper portions 44 defines a nose cutout 46 formed in the nasal opening 42 of the sealing flange 30. The nose cutout 46 is adapted to conform to the nasal bridge of the patient and to allow sealing engagement therebetween.

Referring briefly now to FIG. 9, structural integrity and rigidity of the device is facilitated by means of reinforcing elements 50 or beads disposed locally along an inner corner of the nasal cavity 48 at the junction of the mask sidewall 24 and mask basewall 26. The reinforcing elements 50 maintain the lateral orientation of the mask sidewall 24 relative to the mask basewall 26 and prevent collapse of the mask basewall 26 under the pressure of the nasal mask 10 exerted against the patient's face. In this regard, the reinforcing elements 50 and the relative wall thicknesses 32 of the mask sidewall 24 and basewall 26 allow slight compression of the mask shoulder 28 against the patient's face and accommodate mask-shifting as a result of patient movement. In this regard, the mask body 18 is preferably configured to eliminate the development of pressure points against the patient's face while minimizing leakage between the mask shoulder 28 and patient's face.

Referring more particularly now to FIGS. 8-10, each of the nostril-engaging stems 54 defines a stem axis A. The mask shoulder 28 generally defines a sealing plane C or sealing contour with the stem axis A being preferably oriented in non-perpendicular relation to the sealing plane C or contour. Although the stem axes A are generally oriented non-perpendicularly relative to the sealing plane C, it is contemplated herein that the interface portion 12 and, hence, the nostril-engaging stems 54 are positionable in any orientation relative to the sealing plane C.

Each one of the nostril-engaging stems 54 generally has a proximal end 58 and a distal end 56. The proximal end 58 of each of the stems 54 extends upwardly from the interface portion 12 as best seen in FIG. 9. The distal end 56 includes a flare portion 74 which is preferably sized and configured to sealingly engage the patient's nostril. More specifically, each one of the nostril-engaging stems 54 preferably includes a bulb portion 72 located adjacent to the flare portion 74 and which is sized and configured to facilitate lateral deflection of the nostril-engaging stem 54 for better sealing fit with a variety of patients. In this regard, the combination of the bulb portion 72 and the flare portion 74 act as a bellows such that the distal end 56 of the stem 54 may move laterally relative to the proximal end 58.

The bulb portion 72 may facilitate axial movement of the distal end 56 of the stem 54 by partially expanding and/or partially collapsing on one or opposing sides of the bulb portion 72 in order to provide some degree of flexibility in the spacing of the patient's nostrils from patient-to-patient. In this regard, the bulb portion 72 may facilitate fitment of the stems 54 to patients having nostrils of varying depth. The ability of the bulb portion 72 to allow lateral and/or axial movement of the stems 54 is further facilitated by the annular notch 70 formed on at least one of opposing ends of the bulb portion 72 as shown in FIGS. 9 and 10. The annular notch 70 induces lateral bending of the bulb portion 72 thereabout such that the flare portion 74 may better sealingly engage the patient's nostril.

Regarding the relative length of the nostril-engaging stems 54, it is contemplated that the distal end 56 of each of the stems 54 terminates generally adjacent the sealing plane C or sealing contour of the mask body 18 as best seen in FIG. 10. However, the relative length of the stems 54 from the tapered base portion 64 to the flare portion 74 is preferably such that the stems 54 may be anchored and sealingly-engaged to the nostrils without overly-tightening the nasal mask 10 against the patient's face. In addition, the stems 54 are preferably of a length sufficient to minimize the risk of irritation of the patient's nostrils. In this regard, the nasal mask 10 is preferably formed of a resilient deformable biocompatible polymeric material such as silicon rubber which exhibits favorable flexibility characteristics in order to provide a conformal fit to the patient's facial and nasal contours with an even distribution of pressure at the stems 54 and mask shoulder 28.

Referring still to FIGS. 9-10, it can be seen that the nostril-engaging stems 54 each define the fluid passageway. At the proximal end 58 of the nostril-engaging stem, the fluid passageway 60 may have a generally cylindrical configuration which transitions into a taper section 66 wherein the inner diameter of the fluid passageway 60 reduces to a cylindrical section 68. A second taper section 66 may be provided toward the distal end 56 of the nostril-engaging stem 54 and which ultimately transitions into the bulb portion 72 before terminating at the flare portion 74. Each of the nostril-engaging stems 54 is extended outwardly from the interface portion 12 and defines a gap 62 between an exterior surface of the nostril-engaging stem 54 and the interface portion 12 of the nasal mask 10. The gap 62 may further facilitate lateral movement of the nostril-engaging stems 54 in order to allow conformance to different nostril spacings from patient-to-patient.

Although the nasal mask 10 may be used with a variety of respiratory treatments, it is contemplated that the mask body 18 and stems 54 are specifically configured to collectively provide CPAP therapy to the patient at a supply pressure of up to approximately 120 cm of $H_2O$ and at a flow rate of up to approximately 12 liters per minute. However, it should be noted that the integrated mask body 18 and stems 54 may be configured to supply any pressure at any flow rate dependent upon the particular application of respiratory treatment.

The operation of the integrated nasal mask 10 will now be described with reference to the figures. The nasal mask 10 may be provided as a combination of the mask body 18 and the pair of nostril-engaging stems 54. The mask body 18 is preferably sized and configured to substantially envelope a patient's nose and seal thereagainst. Likewise, the nostril-engaging stems 54 are preferably sized and configured to sealingly engage the patient's nostrils. The nasal mask 10 may further include the interface portion 12 which is preferably sized and configured to frictionally fit within the well portion 104 of the universal interface 100. As can be seen in FIG. 3, the interface portion 12 includes a pair of patient ports 112 which are each sized and configured to be insertable into the fluid passageways 60 formed in the nasal mask 10 when the user interface is positioned within the well portion 104.

Both the pressure and supply tubes 140, 144 as illustrated in FIGS. 1-2 may then be connected to respective ones of the pressure and supply fittings 140, 136 located on opposed sides of the interface body 102. A source of pressurized gas 146 may be supplied to the patient via the pressure tube 142 which then flows into the supply manifold 126 of the interface body 102. Pressure transducers may be placed in fluid communication with the pressure tube 142 such that pressure may be monitored at the patient airway.

The combination nasal mask 10 and universal interface 100 may be mounted to the patient as illustrated in FIGS. 1 and 2. The nasal mask 10 is preferably positioned to anatomically conform to the patient's face and, as was mentioned above, to substantially envelope and seal around a perimeter of the patient's nose. Likewise, the nasal mask 10 is preferably positioned on the patient's face such that the nostril-engaging stems 54 anatomically conform to and are placed in sealing engagement with the patient's nostrils.

Care should be taken to ensure that excessive pressure is not exerted upon the patient's septum via the lower end 22 of the mask body 18. Likewise, care should be taken to ensure that the nostril-engaging stems 54 are not inserted too far up into the patient's nostrils to cause patient discomfort which, over prolonged periods of time, may result in nasal trauma nasal snubbing. Likewise, the mask shoulder 28 is preferably positioned around the patient's nasal bridge to prevent the formation of contusions as a result of excessive pressure applied thereto.

Once properly positioned on a patient's face such that sealing engagement is provided at the mask shoulder 28 as well as at the nostril-engaging stems 54, pressurized gas may be supplied to the patient via the supply tube 144 at the supply port 128. The pressure is supplied to the patient's airway via the nostril-engaging stems 54 and/or the mask body 18. The pressure is preferably provided at greater-than-atmospheric pressure to facilitate spontaneous breathing in the patient. During the inspiration phase, the patient may draw in air at the patient passageways 114 of the universal interface 100. The patient passageways 114 are, in turn, directly connected to corresponding ones of the supply passageways 130 in the universal interface 100. Due to the unique geometry within the interior of the universal interface 100, minimal supplies pressure is required to provide the desired amount of patient pressure at the patient ports 112.

During the inspiratory portion of the breathing cycle, intake of breathing gas and/or atmospheric air is provided through the fluid passageways 60 of the nostril-engaging stems 54, depending on the integrity of the seal between the stems 54 (i.e., the flare portions 74) and the patient's nostrils such that the pressurized gas is delivered through the patient's nose. In the event that the nostril-engaging stems 54 fail to completely seal against the patient's nostrils, the flow of pressurized gas through the fluid passageways 60 is maintained within the nasal cavity 48 of the mask body 18 by the sealing engagement of the mask shoulder 28 to the patient's face.

During the expiratory phase of the breathing cycle, gas (i.e., $CO_2$) that is to be exhausted from the patient's lungs is preferably directed into the fluid passageways 60 of the nostril-engaging stems 54 where it may exit the exhalation passageways of the universal interface 100. In the event that the sealing engagement of the nostril-engaging stems 54 is compromised, exhaled gas which does not flow directly into the fluid passageways 60 of the stems 54 may enter the nasal cavity 48 where it is eventually expelled via the nostril-engaging stems 54.

By specifically configuring the mask body 18 to minimize dead space (i.e., minimize the internal volume of the nasal cavity 48) in addition to optimizing the length of the nostril-engaging stems 54, the nasal mask 10 reduces exhalation resistance. In this regard, the nasal mask 10 reduces the work of breathing by the patient. Furthermore, because of the redundant sealing features (i.e., the nasal mask 10 enveloping the patient's nose and the nostril-engaging stems 54 engaging the patient's nostrils), the risks posed by inadequate pressure at the patient as well as the risk of other health complications resulting from improper fitment of the nasal mask 10 is reduced.

The above description is given by way of example, and not limitation. Given the above disclosure, one skilled in the art could devise variations that are within the scope and spirit of the invention disclosed herein. Furthermore, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An integrated nasal mask adapted for delivering gas to a patient, the nasal mask comprising:
   a mask body defining a nasal cavity;
   an interface portion coupled with said mask body via a connecting web having a lateral notch formed across an upper wall such that said connecting web can flex and allow said interface portion to move relative to said mask body, the upper wall having in cross-section two convex portions positioned on opposing sides of the lateral notch, said interface portion comprising at least one patient port;
   at least one elongate hollow nostril-engaging stem extending outwardly from the nasal cavity and defining a fluid passageway for delivering gas to a nose of said patient, said elongate hollow nostril-engaging stem fluidly coupled with said patient port of said interface portion; and
   wherein said interface portion is configured to couple with a universal interface, said universal interface comprising a supply passageway, a pressure passageway and an exhalation port wherein said elongate hollow nostril-engaging stem is configured to physically secure inside said nose of said patient thereby securing said nasal mask without requiring a head strap.

2. The nasal mask of claim 1 wherein:
   the mask body includes a nasal opening sized and configured to substantially envelope a patient's nose.

3. The nasal mask of claim 2 wherein:
   the mask body includes a mask shoulder extending along a periphery of the nasal opening; and
   the mask shoulder being configured to anatomically conform to a face of the patient.

4. The nasal mask of claim 3 wherein:
   the mask body includes a mask basewall and mask sidewalls extending outwardly from the mask basewall; and
   the mask sidewalls having a reducing wall thickness along a direction from the mask basewall to the mask shoulder such that the mask shoulder is conformable to the patient's face.

5. The nasal mask of claim 4 wherein:
   the mask shoulder includes a sealing flange extending therearound; and
   the sealing flange including a pair of flapper portions disposed on opposing sides of the mask body and being configured to sealingly engage opposing sides of the patient's nose.

6. The nasal mask of claim 4 wherein at least one nostril-engaging stem has a proximal end extending from the nasal cavity and a free distal end having a flare portion sized and configured to sealingly engage the patient's nostril.

7. The nasal mask of claim 6 wherein the at least one nostril-engaging stem further includes a bulb portion located adjacent the flare portion and being sized and configured to facilitate lateral deflection of the flare portion.

8. The nasal mask of claim 4 wherein:
   the stem defines a stem axis;
   the mask shoulder defining a sealing plane; and
   the stem axis being oriented in non-perpendicular relation to the sealing plane.

9. The nasal mask of claim 8 wherein a distal end of the stem terminates adjacent the sealing plane.

10. The nasal mask of claim 1 wherein:
    the mask body and stem are configured to collectively enable continuous positive airway pressure (CPAP) to the patient at a supply pressure of no greater than approximately 120 cm $H_2O$ and a flow rate of up to approximately 12 liters per minute.

11. An integrated nasal mask adapted to be engageable to a universal interface having a pair of patient ports, the nasal mask comprising:
    a mask body defining a nasal cavity;
    an interface portion coupled with said mask body via a connecting web having a lateral notch formed across an upper wall such that said connecting web can flex and allow said interface portion to move relative to said mask body, the upper wall having in cross-section two convex portions positioned on opposing sides of the lateral notch, said interface portion comprising a pair of patient ports;
    a pair of hollow elongate nostril-engaging stems extending outwardly from the nasal cavity of said mask body, each one of the stems being sealingly engageable to said pair of patient ports and defining a fluid passageway for delivering gas to a nose of a patient; and
    wherein said interface portion is configured to couple with a universal interface, said universal interface comprising a supply passageway, a pressure passageway and an exhalation port wherein said elongate hollow nostril-engaging stems are configured to physically secure inside said nose of said patient thereby securing said nasal mask without requiring a head strap.

12. The nasal mask of claim 11 wherein:
    the mask body includes a nasal opening sized and configured to substantially envelope a patient's nose.

13. The nasal mask of claim 12 wherein:
    the mask body includes a mask shoulder extending along a periphery of the nasal opening; and
    the mask shoulder being configured to anatomically conform to a face of the patient.

14. The nasal mask of claim 13 wherein:
    the mask shoulder includes a sealing flange extending therearound; and a pair of flapper portions being disposed on opposing sides of the mask body and being configured to sealingly engage opposing sides of the patient's nose.

15. The nasal mask of claim 13 wherein:
each of the stems defines a stem axis;
the mask shoulder generally defining a sealing plane; and
the stem axes being oriented in non-perpendicular relation to the sealing plane.

16. The nasal mask of claim 12 wherein:
the mask body includes a mask basewall and mask sidewalls extending outwardly from the mask basewall; and
the mask sidewalls having a reducing wall thickness along a direction from the mask basewall to a mask shoulder such that the mask shoulder is conformable to a face of the patient.

17. The nasal mask of claim 11 wherein each one of the stems has proximal and distal ends, the proximal ends being engaged to the nasal cavity, the distal ends terminating in a flare portion, each flare portion sized and configured to sealingly engage one of the patient's nostrils.

18. The nasal mask of claim 17 wherein each one of the stems further includes a bulb portion located adjacent the flare portion and being sized and configured to facilitate lateral deflection of the flare portion.

* * * * *